United States Patent
Tembe et al.

(10) Patent No.: US 6,930,218 B2
(45) Date of Patent: Aug. 16, 2005

(54) PROCESS FOR THE PREPARATION OF LINEAR LOW MOLECULAR WEIGHT OLEFINS BY THE OLIGOMERIZATION OF ETHYLENE

(75) Inventors: Gopal Laxman Tembe, Gujarat (IN); S. Muthukumaru Pillai, Gujarat (IN); M. Ravindranathan, Gujarat (IN)

(73) Assignee: Indian Petrochemicals Corporation Limited, Gujarat (IN)

( * ) Notice: Subject to any disclaimer, the term of this patent is extended or adjusted under 35 U.S.C. 154(b) by 0 days.

(21) Appl. No.: 09/938,122

(22) Filed: Aug. 23, 2001

(65) Prior Publication Data

US 2002/0147375 A1 Oct. 10, 2002

(51) Int. Cl.$^7$ ................................................ C07C 2/26
(52) U.S. Cl. ........................ 585/522; 585/512; 585/523
(58) Field of Search ................................ 585/512, 522, 585/523

(56) References Cited

U.S. PATENT DOCUMENTS 4,409,414 A * 10/1983 Langer, Jr. .................. 585/524
4,855,525 A * 8/1989 Young et al. ................ 585/512
5,260,500 A * 11/1993 Shiraki et al. ............... 585/520

OTHER PUBLICATIONS

Vaartstra, et al., Alcohol Adducts of Alkoxides: Intramolecular Hydrogen Bonding as a General Structural Feature, *Inorganic Chemistry*, vol. 29, 3126–3127, No. 17, 1990.

Kunicki, et al., Studies on the Reaction of Triethylaluminum with Methyl Alcohol, *Bulletin of the Polish Academy of Sciences Chemistry*, vol. 33, No. 5–6, 1985.

* cited by examiner

*Primary Examiner*—Thuan D Dang
(74) *Attorney, Agent, or Firm*—Pillsbury Winthrop Shaw Pittman LLP

(57) ABSTRACT

A process for the preparation of low molecular weight linear alpha olefins is disclosed. The process comprises oligomerising ethylene in an inert aliphatic or aromatic solvent in the presence of a catalyst comprising of a first component selected from zirconium alkoxide and zirconium aryloxide and a second component selected from alkyl aluminum halide and/or alkyl aluminum.

9 Claims, No Drawings

PROCESS FOR THE PREPARATION OF LINEAR LOW MOLECULAR WEIGHT OLEFINS BY THE OLIGOMERIZATION OF ETHYLENE

FIELD OF THE INVENTION

The present invention relates to a process for the preparation of linear low molecular weight alpha olefins by the oligomerization of ethylene. More particularly, the present invention relates to a process for the oligomerization of ethylene to obtain low molecular weight alpha olefins, such as $C_4$ to $C_{24}$, preferably, $C_4$ to $C_{18}$ alpha olefins, using an improved catalyst system comprising of a zirconium alkoxide, and alkylaluminum halide and/or alkylaluminums.

BACKGROUND OF THE INVENTION

Low molecular weight alpha olefins can be synthesised by polymerisation of ethylene. It is known in the art that this process produces even carbon numbered olefins having 4 to 50 carbon atoms and terminal double bonds. In some cases branched olefins are also produced.

Present commercial processes for making $C_4$ to $C_{20}$ linear alpha olefins are based on Ziegler high pressure growth reaction on aluminum triethyl (Ethyl process, U.S. Pat. No. 3,906,053, 1975) followed by low pressure displacement or non-Ziegler route. The Gulf process uses a one step catalytic reaction, wherein chain growth and elimination occur simultaneously in the same reactor (DE 1443927, 1961). In the non-Ziegler route, organo-nickel complexes in combination with a modifier is employed for SHOP process (U.S. Pat. No. 3,676,523, 1972; U.S. Pat. No. 3,726,938, 1973; U.S. Pat. No. 3,825,615, 1974; European Patent 177999, 1986). $ZrCl_4$-$EtAl_2Cl_3$-Thiophene catalyst has been employed in the Idemitsu process (European Patent 241956, 1987; Japanese Patent 6259225, 1987).

The use of $Ti(OR)_4$ (R=Cresyl)-$EtAl_2Cl_3$-$PPh_3$ to obtain better control over distribution of alpha olefins is described in Indian Patent 182153 (1999) and in European Patent 0722922 (1999). The Exxon process (U.S. Pat. No. 4,409,414, 1983 and U.S. Pat. No. 4,486,615, 1984) has shown that at least 90 mole % linear alpha olefins having average molecular weight ranging from 70 to 700 can be obtained from oligomerising ethylene in the presence of $AlEt_2Cl$—$AlEtCl_2$—$TiCl_4$-t-BuOH and $AlEt_2Cl$—$AlEtCl_2$—$ZrCl_4$-n-BuOH catalyst systems.

UOP has developed a process for oligomerization of ethylene using nickel based catalyst in sulfolane solvent (U.S. Pat. No. 4,689,437, 1987). The purity and distribution of alpha olefins are increased by adding 1 to 6 wt % water as an additive.

However, the prior art processes suffered from several disadvantages. For example, the UOP process mentioned above employ very high ethylene pressures, in the range of 95 to 140 atmospheres. Also in this process, the conversion of ethylene drops sharply from 57.8% (0.71% water additive) to 11.3% (4.51% water additive) after $4^{th}$ reaction time. In the Idimetsu process mentioned above, other polymers, apart from alpha olefins are formed. The prior art catalysts system also suffer from a higher deactivation rate.

Therefore, there is an urgent need for an improved process for the preparation of linear low molecular weight alpha olefins in high yields, which also avoids the above-mentioned drawbacks of the prior art. There is also an urgent need to provide a catalyst system, which has a much lower deactivation rate as compared to the prior art catalysts.

OBJECTS OF THE INVENTION

The primary object of the invention is to provide a process for producing linear alpha olefins of low molecular weight, preferably in the range of 56 to 500 from ethylene.

Another object of the invention is to provide an eco-friendly process for the preparation of low molecular weight linear alpha olefins by ethylene oligomerization.

It is yet another object of the invention to provide a process for preparing linear low molecular weight alpha olefins from ethylene using a catalyst system which has a lower deactivation rate.

It is another important object of the present invention to provide an improved process for the preparation of linear low molecular weight alpha olefins in high yields, which also avoids the above-mentioned drawbacks of the prior art.

It is another important object of the present invention to provide an improved process for the preparation of linear low molecular weight alpha olefins, preferably, $C_4$ to $C_{24}$, more preferably, $C_4$ to $C_{18}$ alpha olefins, using an improved catalyst system in high yields, which also avoids the above-mentioned drawbacks of the prior art.

SUMMARY OF THE INVENTION

The above and other objects of the present invention are achieved by process of the present invention by the oligomerization of ethylene using a multicomponent catalyst system essentially comprising of zirconium alkoxide and alkylaluminum halide and/or alkylaluminums.

Accordingly, the present invention provides a process for the preparation of low molecular weight linear alpha olefins having 4 to 24 carbon atoms, comprising oligomerizing ethylene in an inert aliphatic or aromatic solvent in the presence of a catalyst comprising a zirconium component selected from the group consisting of zirconium alkoxide and zirconium aryloxide, and an alkyl aluminum and/or alkyl aluminum halide component.

The solvent is preferably toluene or cyclohexane. N-Octane and any long chain, high boiling aliphatic saturated hydrocarbon may also be conveniently employed. Similarly, instead of toluene, any alkyl substituted aromatic hydrocarbon may be employed as the solvent.

In one embodiment of the invention, the process is carried out under a continuous supply of ethylene and agitation.

In another embodiment of the invention, the process is performed in semi-continuous mode with ethylene being fed continuously during each period of the process.

In another embodiment of the invention, the catalyst system comprises of at least two components, the first component comprising of zirconium (IV) alkoxide/ carboxylate and the second component comprising triethylaluminum and/or ethylaluminum sesquichloride.

In a preferred embodiment of the invention, the catalyst is of the formula $Zr(OR)_4$-$Et_3Al/Et_3Al_2Cl_3$ wherein R is alkyl or aryl.

In a further embodiment of the invention, $Et_3Al$ or $Et_3Al_2Cl_3$ a mixture of $Et_3Al$ and $Et_3Al_2Cl_3$ is reacted with $Zr(OR)_4$ in the mole ratio of 10:1 to 60:1.

In another embodiment of the invention, the ratio of zirconium alkoxide to the free alcohol in the system is in the range of 1:0.33 to 1:2.3.

In a further embodiment of the invention, when $Et_3Al$ and $Et_3Al_2Cl_3$ are used, the $Et_3Al$ diluted in solvent is initially charged into the reactor and then $Et_3Al_2Cl_3$ and other catalyst components are added therein.

In another embodiment of the invention, the ethylene pressure is in the range of 18 to 38 kg/cm$^2$.

In another embodiment of the invention the temperature of the reaction is in the range of 80° C. to 140° C.

In yet another embodiment of the invention, the process is carried out for a time period in the range of 1 hour to 3 hours.

In yet another embodiment of the invention, the solvent used is selected from cyclohexane and toluene.

In yet another embodiment of the invention, the reaction is carried out at an agitator speed of 300 to 1000 rpm.

In another embodiment of the invention, the zirconium component is selected from the group consisting of zirconium tetra cresylate, zirconium tetra dimethyl phenolate, zirconium tetra n-butoxide, zirconium tetra iso-propoxide, zirconium tetra n-propoxide, zirconium tetra butyrate and zirconium tetra isobutyrate.

DETAILED DESCRIPTION OF THE INVENTION

The present invention relates to a process for the preparation of low molecular weight alpha olefins from ethylene in the presence of an inert and eco friendly aliphatic solvent using a multicomponent catalyst system essentially comprising of zirconium alkoxide, alkylaluminum halide/alkylaluminums.

The first component of the catalyst system is Ziconium (IV) alkoxide/carboxylate, while non limiting examples of the second component include triethylaluminum and/or ethylaluminum sesquichloride. A third component, such as thiopene may optionally be used to reduce the chain growth.

The reaction is carried out in a reactor vessel at a temperature in the range of 80° to 140° C. at ethylene pressures of 18 to 35 kg/cm$^2$ at a continuous supply of ethylene. The present invention enables the production of low molecular weight alpha olefins from ethylene in much higher yield due to the slow deactivation rate of the catalyst system of the present invention. It also has a tremendous advantage over the prior art in that it makes it possible for the process to be carried out at a much lower ethylene pressure as compared to the prior art.

The zirconium (IV) component of the catalyst may be represented by the formula Zr(OR)$_4$ wherein R is alkyl or aryl. Zirconium (IV) butoxide and zirconium (IV) isopropoxides are preferred. The amount of free alcohol present in the Zr(OR)$_4$ is critical. Zirconium (IV) carboxylate includes zirconium (IV) octoate. However, a non-limiting list of Zr(OR)$_4$ includes zirconium (IV) cresylate, zirconium (IV) 2,6-dimethyl phenoxide and the like. The preferred second catalyst component is ethylaluminum sesquichloride or a mixture of triethylaluminum and ethylaluminum sesquichloride system.

The molar ratios of the components of the catalyst used in the invention has a bearing on the production of linear oligomers. The optimum ratio of Zr(OR)$_4$ to ethylaluminum sesquichloride or triethylaluminum/ethylaluminum sesquichloride should be between 1:10 to 1:60. The ratio of Zr(OR)$_4$ to free alcohol present in the system is also critical and should ideally be between 1:0.33 to 1:1.3. Below this ratio, part of the catalyst may undergo oligomerization. In the absence of free alcohol, Zr(OR)$_4$ has a tendency to oligomerize itself to give an inorganic oligomer which has no activity for the present invention.

The oligomerization is preferably carried out at a temperature in the range of 65–180° C., the most preferred range being 80–140° C. While the conversion of ethylene is low at a reaction temperature below 80° C., elevation in temperature leads to lower productivity of the catalyst.

The reaction is preferably carried out at a time range of 1 hour to 3 hours, and the preferred agitator speed is in the range of 300 to 1000 rpm, more preferably 500 to 750 rpm. The active catalyst used in the invention is made by mixing Zr(OR)$_4$ and preferably, ethylaluminum sesquichloride. Preferably, the sequence of mixing is by initially adding triethylaluminum and solvent into the reactor followed by Zr(OR)$_4$ and ethylaluminum sesquichloride in that order.

The oligomeric products made by the present invention comprise of C$_4$ to C$_{24}$ alpha olefins. The oligomerization product is isolated using a catalyst quenching procedure comprising adding aqueous alkali or sodium bicarbonate solution followed by water wash and final recovery by distillation.

The process of the present invention is described further hereinbelow with reference to the following examples, which are merely illustrative and should not be construed as limiting the scope of the invention.

EXAMPLE 1

A 600 ml stainless steel reactor activated with high purity N$_2$ for at least 1 h at 140° C. was cooled to 40° C. and charged with 0.5 mmole Zr(O—C$_6$H$_3$(CH$_3$)$_2$)$_4$, 150 ml cyclohexane and 5 mmole of Et$_3$Al$_2$Cl$_3$. The vessel was heated to 90° C. Ethylene was continuously fed at 21 kg/cm$^2$ for a period of 1 h. The temperature rose from 90° C. to 110° C. during the first 5 minutes. The reaction was carried out at 300 rpm. After 1 h the vessel was cooled and the contents quenched with 3 ml of n-butanol. The gas and liquid products were then collected and analyzed by gas chromatograph. The product (19.8 gm) consisted of C$_4$ to C$_{20}$+ olefins and the ethylene conversion was 70.6% (wt). The selectivity of linear olefins was 1-C$_4$=27.7, 1-C$_6$ to 1-C$_{10}$=31.2, 1-C$_{12}$ to 1-C$_{18}$=26.6 and 1.-C$_{20}$+=14.3. The yield of catalyst is 413 g AO/g.Zr.

Table 1 shows the results obtained when Zr(OC$_6$H$_4$CH$_3$)$_4$ is employed as the catalyst.

EXAMPLE 2

A dry 600 ml stainless steel vessel was initially charged with 1.5 mmole of Et$_3$Al in 100 ml cyclohexane. It was stirred for about 10 minutes. Then 4.5 mmole Et3Al$_2$Cl$_3$ and 0.16 mmole Zr(OBu)$_4$. BuOH in 200 ml cyclohexane were added. The autoclave was heated to 100° C. Ethylene was continuously fed at 33 kg/cm$^2$ for a period of 3 h The temperature rose from 100° C. to 125° C. during the first 5 min. The reaction was carried out at 300 rpm. About 103.8 gm of alpha olefins was obtained at an ethylene conversion of 86.2%. The selectivity of linear olefins was 1-C$_4$=40.7, 1-C$_6$ to 1-C$_{10}$=52.7, 1-C$_{12}$ to 1-C$_{18}$=6.3 and 1-C$_{20}$+=0.3. The yield of catalyst is 7206 g AO/g.Zr.

EXAMPLE 3

The procedure of example 2 was followed. In 600 ml vessel were added 0.75 mmole Et$_3$Al, 2.25 mmole Et$_3$Al$_2$Cl$_3$, 0.11 mmole Zr(OBu)$_4$.BuOH and 150 ml cyclohexane. With stirrer speed 300 rpm ethylene was fed at 31 kg/cm$^2$ for 3 h continuously. About 53.6 gm of linear alpha olefins were obtained at an ethylene conversion of 88.6%. The selectivity to linear olefins was 1-C$_4$=43, 1-C$_6$ to 1-C$_{10}$=47.5, 1-C$_{12}$ to 1-C$_{18}$8.7 and 1-C$_{20}$+=0.7. The yield of catalyst is 5150 g AO/g.Zr.

EXAMPLE 4

The procedure of example 1 was followed. In 600 ml reactor were added 5 mmole $Et_3Al_2Cl_3$, 0.38 mmole $Zr(OBu)_4 \cdot BuOH$ and 300 ml cyclohexane. The reactor was maintained at 140° C. while ethylene was fed at 26 kg/cm² for a period of 3h. About 118.7 gms of linear alpha olefins was obtained at an ethylene conversion of 95.7%. The selectivity of linear olefins was $1-C_4=30.9$, $1-C_6$ to $1-C_{10}=49.9$, $1-C_{12}$ to $C_{18}=16.4$ and $1-C_{20}+=2.8$. The yield of catalyst is 3430 g AO/g.Zr.

EXAMPLE 5

The procedure of example 2 was followed. In 600 ml reactor were added 1.62 mmole $Et_3Al$, 4.85 mmole $Et_3Al_2Cl_3$, 0.175 mmole $Zr(OBu)_4 \cdot 0.33BuOH$ and 200 ml cyclohexane. The reactor was maintained at 125° C. while ethylene was fed at 34 kg/cm² for a period of 3 h., The reaction was carried out at 500 rpm. About 165.1 gm of linear olefins was obtained at an ethylene conversion of 94.9%. The selectivity to various olefins were $1-C_4=37.7$, $1-C_6$ to $1-C_{10}=54.9$, $1-C_{12}$ to $1-C_{18}=7$ and $1-C_{20}+=0.3$. The yield of catalyst is 10319 g AO/g.Zr.

EXAMPLE 6

The procedure of example 2 was followed. In 600 ml reactor were added 0.75 mmole $Et_3Al$, 2.25 mmole $Et_3Al_2Cl_3$, 0.12 mmole $Zr(OBu)_4 \cdot BuOH$ and 200 ml cyclohexane. The reactor was maintained at 125° C. while ethylene was fed at 32 kg/cm² for 3h. The reaction was carried out at 750 rpm. About 115.2 gm linear olefins was obtained at an ethylene conversion of 84.7%. The selectivity to various olefins were $1-C_4=33.2$, $1-C_6$ to $1-C_{10}=56$, $1-C_{12}$ to $1-C_{18}=10.3$ and $1-C_{20}+=0.5$. The yield of catalyst is 10666 g AO/g.Zr.

EXAMPLE 7

The procedure of example 2 was followed. In 600 ml reactor were added 1.38 mmole. $Et_3Al$, 4.14 mmole $Et_3Al_2Cl_3$, 0.12 mmole $Zr(OBu)_4 \cdot 1.3tert$-BuOH 0.48 mmole. Thiophene and 200 ml cyclohexane. The reactor was maintained at 125° C. while ethylene was fed at 34 kg/cm² for a period of 3 h. The reaction was carried out at 750 rpm. About 75.2 gm linear olefins was obtained at an ethylene conversion of 85.5%. The selectivity to various olefins were $1-C_4=47.5$, $1-C_6$ to $1-C_{10}=47.5$, $1-C_{12}$ to $1-C_{18}32$ 4.9. The yield of catalyst is 6876 g AO/g.Zr.

EXAMPLE 8

The procedure of example 2 was followed. In 600 ml reactor were added 1.6 mmole $Et_3Al$, 4.8 mmole $Et_3Al_2Cl_3$, 0.16 mmole $Zr(OOCC_3H_7)_4$ and 200 ml of toluene. reactor was maintained at 100° C. while ethylene was fed at 36.5 kg/cm² for a period of 3 h. The reaction was carried out at 500 rpm. About 177.6 gm of linear olefins was obtained at an ethylene conversion of 89.7%. The selectivity to various olefins were $1-C_4=36$, $1-C_6$ to $1-C_{10}=55.7$, $1-C_{12}$ to $1-C_{18}=8$ and $1-C_{20}+=0.3$. The yield of catalyst is 12200 g AO/gZr.,

EXAMPLE 9

The procedure of example 2 was followed. In a 600 ml reactor were added 0.16 mmole $Et_3Al$, 4.8 mmole $Et_3Al_2Cl_3$, 0.2 mmole $Zr(OOCC_3H_7iso)_4$ and 200 ml toluene. The reactor was maintained at 100° C. while ethylene was fed at 33 kg/cm² for a period of 3 h at 300 rpm agitation. About 103.4 gm linear olefins was obtained at an ethylene conversion of 80.7%. The selectivity to various olefins were $1-C_4=36.2$, $1-C_6$ to $1-C_{10}=53$, $1-C_{12}$ to $1-C_{18}=10$ and $1-C_{20}+=0.6$. The yield of catalyst is 5744 gm AO/g.Zr.

EXAMPLE 10

The procedure of example 2 was followed. In a 600 ml reactor were added 1.6 mmole $Et_3Al$, 4.78 mmole $Et_3Al_2Cl_3$, 0.12 mmole $Zr(OOCC_7H_{15})_4$ and 200 ml toluene. The reactor was maintained at 100° C. while ethylene was fed at 36 kg/cm² for a period of 3 h at 500 rpm agitation. About 86 gm linear olefins was obtained at an ethylene conversion of 66.1%. The selectivity to various olefins were $1-C_4=40$; $1-C_6$ to $1-C_{10}=55$ and $1-C_{12}$ to $1-C_{18}=5$. The yield of catalyst is 8970 gm AO/g.Zr.

The catalyst system employed in the process of present invention and illustrated in examples 1 to 10 are influenced by various reaction conditions (Table 2 & 3)

TABLE 1

| Zirconium catalyst mmole | EASC/ TEAL mmole | Al/Zr mole/ mole | Reaction conditions | Alphaolefin. distribution, wt % C4/C6–C10/C12–C18/C20+ | Conv. ethylene % | Productivity g/g · Zr |
|---|---|---|---|---|---|---|
| $Zr(cresyl)_4$ 0.5 | 5.3/— | 10.6 | n-octane(50 ml)/ 100° C./21 kg/cm² $C_2H_4$/0.5 h/ 300 Rpm | 36.2/39.6/21.4/2.8 | 25 | 92.3 |
| $Zr(cresyl)_4$ 0.5 | 5.3/— | 10.6 | Cyclohexane(150)/ 100/21/0.5/300 | 42.6/32.6/19.8/4.5 | 39 | 138.6 |
| $Zr(cresyl)_4$ 1 | 7.5/2.5 | 10 | Cyclohexane(300)/ 100/21/1/300 | 34.5/50.8/13.7/1 | 38.4 | 204 |

TABLE 2

| Zirconium catalyst mmole | TEAL/ EASC mmole | Al/Zr mole/ mole | Reaction conditions | Alphaolefin. distribution, wt % C4/C6–C10/C12–C18/C20+ | Conv. ethylene % | Productivity g/g · Zr |
|---|---|---|---|---|---|---|
| $Zr(OBu)_4 \cdot$ BuOH | —/9 | 18 | Cyclohexane(300 ml)/110° C./21 | 33.2/57.5/8.8/0.3 | 68.5 | 1225 |

TABLE 2-continued

| Zirconium catalyst mmole | TEAL/ EASC mmole | Al/Zr mole/ mole | Reaction conditions | Alphaolefin. distribution, wt % C4/C6–C10/C12–C18/C20+ | Conv. ethylene % | Productivity g/g · Zr |
|---|---|---|---|---|---|---|
| 0.5 | | | kg/cm$^2$C$_2$H$_4$/1 h/ 300 rpm | | | |
| Zr(OBu)$_4$. BuOH 0.5 | —/5 | 10 | Cyclohexane(300)/ 110/19/1/300 | 29.8/47.8/19.3/3.0 | 95.5 | 2518 |
| Zr(OBu)$_4$. BuOH 0.5 | —/5 | 10 | Cyclohexane(300)/ 125/21/2.5/300 | 11.6/52.1/29.2/7.5 | 94 | 2827 |
| Zr(OBu)$_4$. BuOH 0.3 | 1.5/4.5 | 20 | Cyclohexane(300)/ 125/32/3/300 | 27.5/49.7/19.7/3.1 | 95.2 | 6131 |
| Zr(OBu)$_4$. BuOH 0.25 | 1.6/4.8 | 26 | Cyclohexane(300)/ 125/30/3/300 | 26.4/57.2/15.4/1 | 86.4 | 5888 |
| Zr(OBu)$_4$. BuOH 0.144 | 1.62/4.86 | 45 | Cyclohexane(300)/ 125/33/3/300 | 49.2/44.7/6/— | 81 | 5623 |
| Zr(OBu)$_4$. BuOH 16 | 1.6/4.8 | 40 | Cyclohexane(200)/ 125/35/3/500 | 30/51.1/17.4/1.4 | 82.2 | 7882 |
| Zr(OBu)$_4$. BuOH 0.1 | 1.5/4.5 | 60 | Cyclohexane(200)/ 125/33/3/500 | 42.3/51.3/6.3/0.1 | 80.2 | 8872 |
| Zr(OBu)$_4$. BuOH 0.1 | 0.75/2.25 | 30 | Cyclohexane(200)/ 125/35/3/1000 | 39.9/52.1/7.4/0.3 | 82.8 | 8286 |
| Zr(OBu)$_4$. BuOH 0.055 | 0.75/2.25 | 54 | Cyclohexane(200)/ 125/34/3/500 | 53.8/41.1/5.0/0.05 | 73.2 | 8500 |

TABLE 3

| Zirconium catalyst mmole | TEAL/ EASC mmole | Al/Zr mole/ mole | Reaction conditions | Alphaolefin. distribution, wt % C4/C6–C10/C12–C18/C20+ | Conv. ethylene % | Productivity g/g · Zr |
|---|---|---|---|---|---|---|
| Zr(OBu)$_4$. 0.33 BuOH 0.284 | 1.35/4.05 | 19 | Cyclohexane (300 ml)/125 ° C./29.5 kg/ cm$^2$C$_2$H$_4$/3 h/ 500 rpm | 36.5/42.9/19.6/0.9 | 94.2 | 6454 |
| Zr(OBu)$_4$. 0.33 BuOH 0.125 | 1.56/4.7 | 50 | Cyclohexane (200)/125/32/ 3/750 | 41.7/51.3/6.9/0.1 | 94.3 | 12198 |
| Zr(OBu)$_4$. 1.3 tert.BuOH 0.294 | 1.62/4.85 | 22 | Cyclohexane (300)/125/33.5/ 3/300 | 29.9/56.6/11.7/1.3 | 80.6 | 4104 |
| Zr(OBu)$_4$. 0.4 tert.BuOH 0.13 | 1.6/4.8 | 50 | Cyclohexane/ 80/38/200/3/ 500 | 49.9/48.6/1.5/— | 64.7 | 5310 |
| Zr(OPr.i)$_4$. 2.3 iso.PrOH 0.14 | 1.47/4.41 | 42 | Cyclohexane (200)/125/35/ 3/500/Thiophene 0.42 mmole | 50.3/44.7/4.9/— | 80 | 4583 |
| Zr(OPr.i)$_4$. 2.3 isoPrOH 0.37 | —/4.8 | 13 | Cyclohexane (300)/125/32/ 3/300 | 16.1/29.4/34.3/20 | 85.5 | 2934 |

TEAL = Et$_3$Al; EASC = Et$_3$Al$_2$Cl$_3$.

We claim:

1. An ecologically friendly process of catalytic oligomerization of ethylene to low molecular weight alpha olefins, comprising the steps of:

(i) adding to a reactor a catalytic component comprising an alkyl aluminum and a solvent selected from toluene, cyclohexane, and n-octane;

(ii) admixing is said reactor a catalytic component comprising a Zr(OR)$_4$ compound in an alkanol at a ratio ranging from 1:0.33 to 1:1.23, wherein R s alkyl or aryl (iii) and further admixing in said reactor a catalytic component comprising alkyl aluminum halide; and (iv) charging the reactor continuously with ethylene at a pressure ranging from 18 to 35 kg/cm$^2$ at a temperature ranging from 80 to 140° C. and with a constant agitation to oligomerizing the ethyiore to low molecular weight alpha olefins.

2. The process as claimed in claim 1 wherein the process is performed in semi-continuous mode with ethylene being fed continuously during each period of the process sufficient for preparing a batch of the olefins.

3. The process as claimed in claim 1 wherein the mole ratio of the components in steps (f) and (iii) to the component in step (ii) ranges front 10:1 to 60:1.

4. The process as claimed in claim 1 wherein, the process is carried out for a time period in the range of 1 hour to 3 hours.

5. The process as claimed in claim 1 wherein the oligomerization reaction is carried out at an agitator speed of 300 to 1000 rpm.

6. The process as claimed in claim 1 wherein, the zirconium component is selected from the group consisting of zirconium tetra cresylate, zirconium tetra-dimethyl phenolate, zirconium tetra n-butoxide, zirconium tetra isopropoxide, zirconium tetra n-propoxide, zirconium tetrabutyrate and zirconium tetra isobutyrate, each in the presence of an alcohol at a ratio of 1:0.33 to 1:1.23.

7. The process as claimed in claim 1 wherein the process includes an addition of a thiophene to reduce or limit chain growth.

8. The process as claimed in claim 1 wherein said alkyl aluminum of step (i) is selected from the group consisting of: ethyl aluminum and triethyl aluminum; and wherein said alkyl aluminum halide is ethyl aluminum sesquichloride.

9. The process of claim 1 wherein the catalytic component of step (ii) consists of $Zr(OBu)_4$ in BuOH having a mole ratio of 1:0.33 to 1:1.23.

* * * * *